(12) United States Patent
Liu et al.

(10) Patent No.: US 11,427,516 B2
(45) Date of Patent: Aug. 30, 2022

(54) MULTISTAGE NANOREACTOR CATALYST AND PREPARATION AND APPLICATION THEREOF

(71) Applicant: Jiangnan University, Wuxi (CN)

(72) Inventors: Xiaohao Liu, Wuxi (CN); Yuebing Xu, Wuxi (CN); Feng Jiang, Wuxi (CN); Bing Liu, Wuxi (CN); Dapeng Liu, Wuxi (CN); Ting Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 55 days.

(21) Appl. No.: 16/952,183

(22) Filed: Nov. 19, 2020

(65) Prior Publication Data
US 2021/0070672 A1    Mar. 11, 2021

Related U.S. Application Data

(60) Division of application No. 16/201,060, filed on Nov. 27, 2018, now Pat. No. 10,875,817, which is a
(Continued)

(30) Foreign Application Priority Data

Jul. 5, 2017 (CN) .......................... 201710542897.4

(51) Int. Cl.
*C07C 1/04* (2006.01)
*B01J 35/00* (2006.01)
(Continued)

(52) U.S. Cl.
CPC ............. *C07C 1/0445* (2013.01); *B01J 21/04* (2013.01); *B01J 21/08* (2013.01); *B01J 23/78* (2013.01);
(Continued)

(58) Field of Classification Search
CPC ... B01J 21/04; B01J 21/08; B01J 23/78; B01J 23/8892; B01J 29/064; B01J 35/0006;
(Continued)

(56) References Cited

U.S. PATENT DOCUMENTS 3,145,183 A * 8/1964 Fisher .................... B01J 37/024
                                                    502/527.15
3,259,589 A * 7/1966 Michalko ................. B01J 35/08
                                                    502/333
(Continued)

FOREIGN PATENT DOCUMENTS

CN         10 4549447      * 4/2015  ............ B01J 29/072
CN         10 5728020      * 7/2016  ............. B01J 29/46
(Continued)

OTHER PUBLICATIONS

Jinjing Li et al., "Direct conversion of syngas into hydrocarbons over a core-shell Cr—Zn@SiO2@SAPO-34 catalyst." Chinese Journal of Catalysis 36, pp. 1131-1135. (Year: 2015).*

*Primary Examiner* — Patricia L. Hailey
(74) *Attorney, Agent, or Firm* — IPro, PLLC

(57) ABSTRACT

The present disclosure discloses a multistage nanoreactor catalyst and preparation and application thereof, belonging to the technical field of synthesis gas conversion. The catalyst consists of a core of an iron-based Fischer-Tropsch catalyst, a transition layer of a porous oxide or porous carbon material, and a shell layer of a molecular sieve having an aromatization function. The molecular sieve of the shell layer can be further modified by a metal element or a non-metal element, and the outer surface of the molecular sieve is further modified by a silicon-oxygen compound to adjust the acidic site on the outer surface and the aperture of the molecular sieve, thereby inhibiting the formation of heavy aromatic hydrocarbons. According to the disclosure, the shell layer molecular sieve with a transition layer and a
(Continued)

shell layer containing or not containing auxiliaries, and with or without surface modification can be prepared by the iron-based Fischer-Tropsch catalyst through multiple steps. The catalyst can be used for direct preparation of aromatic compounds, especially light aromatic compounds, from synthesis gas; the selectivity of light aromatic hydrocarbons in hydrocarbons can be 75% or above, and the content in the liquid phase product is not less than 95%; and the catalyst has good stability and good industrial application prospect.

10 Claims, 1 Drawing Sheet

Related U.S. Application Data continuation of application No. PCT/CN2017/119419, filed on Dec. 28, 2017.

(51) Int. Cl.

| | |
|---|---|
| *B01J 37/02* | (2006.01) |
| *B01J 37/06* | (2006.01) |
| *B01J 21/08* | (2006.01) |
| *B01J 23/78* | (2006.01) |
| *B01J 21/04* | (2006.01) |
| *B01J 29/064* | (2006.01) |
| *B01J 37/03* | (2006.01) |
| *B01J 37/00* | (2006.01) |
| *B01J 37/08* | (2006.01) |
| *B01J 37/30* | (2006.01) |
| *B01J 23/889* | (2006.01) |

(52) U.S. Cl.
CPC ......... *B01J 23/8892* (2013.01); *B01J 29/064* (2013.01); *B01J 35/0006* (2013.01); *B01J 35/0086* (2013.01); *B01J 37/0018* (2013.01); *B01J 37/0203* (2013.01); *B01J 37/024* (2013.01); *B01J 37/0205* (2013.01); *B01J 37/0236* (2013.01); *B01J 37/031* (2013.01); *B01J 37/06* (2013.01); *B01J 37/08* (2013.01); *B01J 37/30* (2013.01); *C07C 1/044* (2013.01); *B01J 2229/186* (2013.01); *C07C 2521/04* (2013.01); *C07C 2521/08* (2013.01); *C07C 2523/04* (2013.01); *C07C 2523/34* (2013.01); *C07C 2523/745* (2013.01); *C07C 2523/78* (2013.01); *C07C 2523/889* (2013.01); *C07C 2529/06* (2013.01); *Y02P 20/52* (2015.11)

(58) Field of Classification Search
CPC ............... B01J 35/0086; B01J 37/0018; B01J 37/0203; B01J 37/0205; B01J 37/0236; B01J 37/024; B01J 37/031; B01J 37/06; B01J 37/08; B01J 37/30; B01J 2229/186
USPC .................. 502/300, 325, 338; 428/403–405
See application file for complete search history.

(56) References Cited

U.S. PATENT DOCUMENTS

| | | | | |
|---|---|---|---|---|
| 4,804,796 A | * | 2/1989 | Wang ..................... | B01J 35/08 585/277 |
| 5,763,351 A | * | 6/1998 | Ichimura ................ | C10G 35/06 428/404 |
| 7,442,365 B1 | * | 10/2008 | Jacobsen .................. | B01J 37/10 423/709 |
| 9,108,181 B2 | * | 8/2015 | Stockwell ............ | B01J 37/0246 |
| 2014/0171297 A1 | * | 6/2014 | Goia ...................... | B01J 23/892 977/773 |

FOREIGN PATENT DOCUMENTS

| | | | | |
|---|---|---|---|---|
| CN | 10 6994366 | * | 8/2017 | ............. B01J 29/85 |
| JP | 2011-184573 | * | 9/2011 | ............. C10G 2/00 |

* cited by examiner

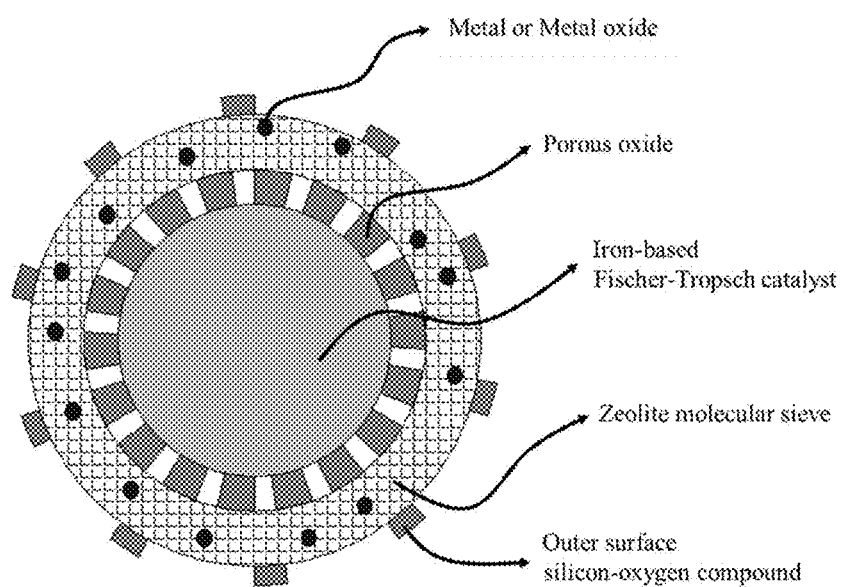

MULTISTAGE NANOREACTOR CATALYST AND PREPARATION AND APPLICATION THEREOF

TECHNICAL FIELD

The disclosure herein relates to a multistage nanoreactor catalyst and preparation and application thereof, in particular to a multistage nanoreactor catalyst for directly preparing aromatic compounds from synthesis gas and preparation and application thereof, belonging to the technical field of synthesis gas conversion.

BACKGROUND

Aromatic compounds including benzene, toluene and xylene (BTX) are important chemical basic raw materials, mainly derived from petroleum-based production processes, such as naphtha steam cracking for producing ethylene and catalytic reforming or cracking for producing gasoline and diesel. With the light weight of olefin raw materials, the reduction of crude oil resources and the increasingly prominent environment issues, the acquisition of aromatic compounds from petroleum has been challenged and unsustainable. Therefore, the non-petroleum route to prepare aromatic hydrocarbons has received more and more attention.

Based on China's energy structure of rich coal and poor petroleum, China has been supporting the development of new technologies for producing various chemical products using coal and biomass as raw materials in the past decade, from the perspective of energy strategy and safety, so as to reduce the dependence on petroleum. As the coal gasification process approaches maturity, the direct preparation of aromatic hydrocarbons from synthesis gas as an alternative technical route for producing BTX is of great significance for utilizing China's rich coal resources and relieving the dependence on petroleum resources. The process does not require further preparation of aromatic hydrocarbons from synthesis gas through methanol or dimethyl ether as in an indirect process, so that the process is simplified, the operating cost is low, and the investment is greatly reduced.

At present, the direct preparation of aromatic hydrocarbons from synthesis gas is mainly implemented by placing two catalysts having a synthesis gas conversion function and a dehydro-aromatization function in a tandem double-bed reactor sequentially or placing the same into a single-bed reactor in an inter-particle or intra-particle mixing manner. For example, the two-stage reactor used in Shanxi Coal Chemical Plant of China is respectively charged with two types of catalysts, which can convert the synthesis gas into aromatic hydrocarbons through dimethyl ether. In addition, the Guan Naijia research group in Nankai University reported that the Fischer-Tropsch synthesis (FTS) catalyst Fe/MnO was physically mixed with the Ga/HZSM-5 catalyst, and the aromatic hydrocarbon selectivity was close to 50% under 1.1 MPa at 270° C.

However, direct composite catalysts have certain limitations for the direct preparation of aromatic hydrocarbons from synthesis gas. For example, intermediates that are susceptible to aromatization, such as C2~C5, still need to undergo several times of diffusion to enter the active centers of the aromatization catalysts for activation and reaction. At the same time, these intermediates have the opportunity to escape. Meanwhile, after CO undergoes a CO conversion catalyst, the CO often cannot continue to activate and react on a second catalyst. Moreover, the physical mixing easily causes non-uniform distribution of two active site concentrations in the reaction system, which will affect the aromatization reaction of the intermediates to varying degrees. In the presence of these problems, the ultimate aromatic hydrocarbon selectivity and yield are generally not high, especially light aromatic hydrocarbons such as benzene, toluene and xylene.

SUMMARY

In view of the problems in the conventional catalysts, the present disclosure relates to a multistage nanoreactor catalyst capable of realizing one-step high-selectivity preparation of aromatic compounds from synthesis gas, as well as preparation and application thereof in reactions of preparation of aromatic compounds from synthesis gas. The designed catalyst has high aromatic hydrocarbon selectivity, especially for light aromatic hydrocarbons, and is expected to be applied industrially.

The catalyst according to the present disclosure is a multistage nanoreactor catalyst for directly preparing aromatic compounds from synthesis gas, and the multistage nanoreactor catalyst is composed of a structure of a core layer, a shell layer and a core-shell transition layer (as shown in FIG. 1). The core layer is an iron-based catalyst having Fischer-Tropsch activity for activating CO, $CO_2$ and $H_2$ and forming a main product of olefin, the weight of the core layer being 0.1% to 80% of the total weight of the catalyst; the shell layer is a molecular sieve for forming an aromatic hydrocarbon product, the weight of the shell layer being 0.1% to 80% of the total weight of the catalyst; and the core-shell transition layer is a porous oxide or porous carbon material, the weight of the transition layer being 0.01% to 35% of the total weight of the catalyst.

In one embodiment of the present disclosure, the iron-based catalyst having Fischer-Tropsch activity may be a supported or unsupported catalyst, and contains or does not contain additives.

In one embodiment of the present disclosure, the molecular sieve is one or a mixture of two or more of ZSM-5, MCM-22, MCM-49, and SAPO-34 zeolite molecular sieve materials.

In one embodiment of the present disclosure, the molecular sieve may or may not contain additives.

In one embodiment of the present disclosure, the outer surface of the molecular sieve has or does not have a silicon-oxygen compound.

In one embodiment of the present disclosure, the silica-alumina ratio of the zeolite molecular sieve is preferably 10 to 500; when additives are added, the additives are one or more of P, V, Cr, Mn, Fe, Co, Cu, Zn, Ga, Ge, Zr, Mo, Ru, Pd, Ag, W and Re, and the weight of the additives is 0.01% to 35% of the weight of the shell layer based on atoms; and the weight of the silicon-oxygen compound on the outer surface of the molecular sieve is 0.01% to 20% of the weight of the shell layer.

In one embodiment of the present disclosure, the porous oxide of the transition layer is one or more of silicon oxide, aluminum oxide, zirconium oxide, magnesium oxide, zinc oxide, titanium oxide and calcium oxide, and the thickness of the transition layer is 0.1 to 1000 nm, preferably 0.5 to 100 nm.

A preparation method of the catalyst according to the present disclosure comprises the following steps:

step 1, admixing a prepared iron-based catalyst into an organic solvent containing a transition layer oxide precursor, continuously stirring for 0 to 24 h, then performing rotary evaporation to remove the solvent and drying at 30 to 250° C. for 0 to 24 h to obtain a sample;

step 2, admixing the sample prepared in step 1 into an alkaline solution containing a template, a silicon source and an aluminum source, and stirring for 0 to 24 h, wherein the weight ratio of the sample, the template, the silicon source, the aluminum source, alkali and water is (0.5-50):(0.05-1):1:(0.01-1):(0.001-0.5):(10-500); then charging into a hydrothermal kettle, sealing, heating to 110 to 300° C., and hydrothermally crystallizing for 5 to 120 h; filtering a solid product after crystallization and cooling, washing till the pH value of washing liquid is 4 to 11, then drying at 30 to 200° C. for 0 to 24 h, and calcining at 300 to 800° C. for 0 to 24 h to obtain a powder sample;

step 3, admixing the powder obtained in step 2 into a solution containing a soluble salt of a metal element by an incipient wetness impregnation method or an ion exchange method or an excess impregnation method, the soluble salt being preferably one or more of nitrate, carbonate, acetate, sulfate, molybdate, tungstate and chloride; and step 4, admixing the sample powder obtained in step 3 into an organic solvent containing a silicon source, stirring, then removing the solvent by rotary evaporation and drying at 30 to 250° C. for 0 to 24 h, and finally calcining at 350 to 650° C. for 0 to 24 h, wherein the content of the silicon source being 0.01 to 20%.

In one embodiment of the present disclosure, in step 1, the organic solvent is one or more of ethanol, propanol, acetone, cyclohexane, n-hexane, n-heptane and n-pentane.

In one embodiment of the present disclosure, in step 2, the adopted template is one or more of tetrapropylammonium hydroxide, n-propylamine, isopropylamine, hexamethyleneimine, triethylamine and tetraethylammonium hydroxide; the silicon source is one or more of silicon oxide, sodium silicate, propyl orthosilicate, hexamethyldisiloxane, ethyl orthosilicate and isopropyl orthosilicate; the aluminum source is one or more of alumina, aluminum isopropoxide trihydrate, sodium aluminate, aluminum sulfate, boehmite and gibbsite; and the alkali is one or more of sodium hydroxide, potassium hydroxide, potassium carbonate, sodium carbonate, sodium bicarbonate, potassium bicarbonate and sodium acetate.

The present disclosure also provides a method of applying the catalyst to direct preparation of aromatic compounds from synthesis gas.

The catalyst needs to be pre-reduced before use: the pretreatment reducing atmosphere is one or more of hydrogen, carbon monoxide, methane, ethane and ethylene gas; the pretreatment temperature is 150 to 600° C., preferably 280 to 450° C.; the pretreatment pressure is 0.1 to 3 MPa, preferably 0.1 to 1 MPa; the volume space velocity of the pretreatment gas is 1000 to 50000 h$^{-1}$, preferably 1500 to 20000 h$^{-1}$; and the pretreatment time is 1 to 24 h, preferably 1 to 6 h.

The reaction condition suitable for the catalyst is: the reaction gas contains a gas mixture of one or two of carbon monoxide and carbon dioxide, and hydrogen; the volume fraction of hydrogen is 5% to 85%; the reaction temperature is 150 to 600° C., preferably 250 to 450° C.; the reaction pressure is 0.1 to 5 MPa, preferably 0.2 to 2.5 MPa; and the reaction space velocity is 500 to 50000 h$^{-1}$, preferably 1500 to 20000 h$^{-1}$.

The reaction using the catalyst of the present disclosure can be carried out in a fixed bed, fluidized bed or slurry bed reactor, preferably a fixed bed or fluidized bed reactor.

The present disclosure has the following advantages:

(1) The multistage nanoreactor catalyst prepared in the present disclosure can effectively avoid the influence of the shell layer molecular sieve on the core layer catalyst, improve the conversion rate of CO and promote further conversion of the olefin. The catalyst prepared in the present disclosure is suitable for the reaction processes for directly preparing aromatic hydrocarbons using coal-based, biomass-based and natural gas-based synthesis gas as raw materials, particularly for the reaction of preparing light aromatic compounds; the selectivity of light aromatic hydrocarbons in hydrocarbons is up to 75% or above, and the content in the liquid phase product is not less than 95%.

(2) The multistage nanoreactor catalyst prepared in the present disclosure has relatively high aromatic hydrocarbon selectivity, especially the selectivity to light aromatic hydrocarbons, can better inhibit heavy and polycyclic aromatic hydrocarbon such as naphthalene, and has relatively low methane selectivity.

(3) The catalyst has good stability and good industrial application prospect.

BRIEF DESCRIPTION OF FIGURES

FIG. 1 is a schematic diagram showing the structure of a multistage nanoreactor catalyst in an embodiment of the present disclosure.

DETAILED DESCRIPTION

Examples 1~6: Preparation of Multistage Nanoreactor Catalyst for Direct Conversion of Synthesis Gas to Aromatic Compounds Product analysis: the products left from the reactor were condensed in a cold trap, while the uncondensed components were analyzed on-line by a gas chromatography with TCD and FID detectors. In detail, the unreacted CO, formed $CO_2$ and $CH_4$, and inert gas $N_2$ were separated by a packed column of TDX-01 and detected by TCD, and the $N_2$ was used as internal standard substance for calculation of CO conversion. C1-C5 hydrocarbons were separated using an HP-PLOT/$Al_2O_3$ capillary column. The condensed hydrocarbons were collected after reaction and analyzed by another gas chromatography off-line which connected with an FID and a capillary column of HP-1 or FFAP for further separation of para-, ortho- and meta-xylene.

(1) The total CO conversion $X_{CO}$ was calculated as:

$$X_{CO} = ((A_{CO}/A_{N_2})_{in} - (A_{CO}/A_{N_2})_{out})/(A_{CO}/A_{N_2})_{in} \times 100$$

where $(A_{CO}/A_{N_2})_{in}$ and $(A_{CO}/A_{N_2})_{out}$ are the peak area ratio of CO to $N_2$ at the inlet and outlet of reactor, respectively.

The selectivity of CO converted to $CO_2$ ($S_{CO\ to\ CO_2}$) was calculated as:

$$S_{CO\ to\ CO_2} = \{(A_{CO_2}/A_{N_2})_{out} \times f_{CO_2} / ((A_{CO}/A_{N_2})_{in} - (A_{CO}/A_{N_2})_{out}) \times f_{CO}\} \times 100$$

where $(A_{CO_2}/A_{N_2})_{out}$ is the peak area ratio of $CO_2$ to $N_2$. $f_{CO_2}$ and $f_{CO}$ are the correction factors of $CO_2$ and CO, respectively.

(3) The selectivity of CO converted to hydrocarbons ($S_{CO\ to\ HC}$) was calculated as:

$$S_{CO\ to\ HC} = 100 - S_{CO\ to\ CO_2}$$

Definitely, the $CO_2$-free selectivities of CO converted to $CH_4$, $C_2$-$C_6$ in gas phase, and hydrocarbons in liquid phase, namely the $CO_2$-free hydrocarbon distribution, were calculated as:

a) The $CO_2$-free selectivity of CO converted to $CH_4$ was calculated as:

$$S_{CO\ to\ CH_4} = (A_{CH_4}/A_{N_2})_{out} \times f_{CH_4}/((A_{CO}/A_{N_2})_{in} - (A_{CO}/A_{N_2})_{out}) \times f_{CO}) \times 100/S_{CO\ to\ HC}$$

Where $S_{CO\ to\ CH_4}$ is the selectivity of $CH_4$. $(A_{CH_4}/A_{N_2})_{out}$ is the on-line TCD peak area ratio of $CH_4$ to $N_2$. $f_{CH_4}$ is the correction factor of $CH_4$.

b) The $CO_2$-free selectivities of CO converted to $C_2$-$C_6$ hydrocarbons in gas phase were calculated as:

$$S_{CO\ to\ C_n} = A_{C_n}^{FID1} \times f_{C_n}^{FID1}/(A_{CH_4}^{FID1} \times f_{CH_4}^{FID1}) \times S_{CO\ to\ CH_4}$$

Where $A_{C_n}^{FID1}$ and $A_{CH_4}^{FID1}$ are the on-line FID peak areas of $C_n$ (n=2-6) and $CH_4$, respectively; $f_{C_n}^{FID1}$ and $f_{CH_4}^{FID1}$ are the correction factors of $C_n$ (n=2-6) and $CH_4$ in on-line FID, respectively.

a) The $CO_2$-free selectivities of CO converted to total hydrocarbons in liquid phase were calculated as:

$$S_{CO\ to\ C_{liquid\ phase}} = 100 - S_{CO\ to\ CH_4} - \Sigma_{n=2}^{6} S_{CO\ to\ C_n}$$

b) The $CO_2$-free selectivities of CO converted to detailed hydrocarbons in liquid phase were calculated as:

$$S_{CO\ to\ C_n} = A_{C_n}^{FID2} \times f_{C_n}^{FID2}/\Sigma_{n=5}^{n} A_{C_n}^{FID2} \times f_{C_n}^{FID2} \times S_{CO\ to\ C_{liquid\ phase}}$$

Where $A_{C_n}^{FID2}$ is the off-line FID peak area of $C_n$ (n>=5); $f_{C_n}^{FID2}$ is the correction factors of $C_n$ (n>=5) 4 in off-line FID.

Example 1

Dissolve 200.0 g of ferric nitrate nonahydrate and 5.92 g of manganese nitrate hexahydrate into 500 mL of deionized water, precipitate by using 6 mol/L ammonia water as a precipitant at pH=8.0, age, filter, wash and dry at 120° C. for 12 h, and finally calcine at 500° C. for 5 h to obtain a precipitated FeMn catalyst having an iron-manganese atomic ratio of 96 to 4.

Admix 5.0 g of the prepared FeMn catalyst into 50 mL of ethyl orthosilicate solution, continuously stir, then perform rotary evaporation to remove the solvent, dry and calcine to obtain a sample having a $SiO_2$ coating. Next, admix the sample into 50 mL of solution containing tetrapropylammonium hydroxide template, ethyl orthosilicate, $Al_2O_3$, NaOH and $H_2O$ in a ratio of 0.3:1.0:0.03:0.015:130, stir for 4 h, then charge into a hydrothermal kettle, seal, heat to 180° C., and hydrothermally crystallize for 48 h. Filter the solid product after crystallization and cooling, wash till the pH value of the washing liquid is 8, then dry at 120° C. for 12 h, and calcine at 500° C. for 5 h to obtain a catalyst sample A with the weight percentage of a core layer being 66%, the weight percentage of a transition layer being 9% and the weight percentage of a shell layer being 25%.

Example 2

Admix 5 g of the precipitated FeMn catalyst prepared in Example 1 into 50 mL of aluminum isopropoxide trihydrate solution, continuously stir, then perform rotary evaporation to remove the solvent, dry and calcine to obtain a sample having an $Al_2O_3$ coating. Next, admix the sample into 50 mL of solution containing tetrapropylammonium hydroxide template, ethyl orthosilicate, $Al_2O_3$, NaOH and $H_2O$ in a ratio of 0.3:1.0:0.03:0.015:130, stir for 4 h, then charge into a hydrothermal kettle, seal, heat to 180° C., and hydrothermally crystallize for 48 h. Filter the solid product after crystallization and cooling, wash till the pH value of the washing liquid is 8, then dry at 120° C. for 12 h, and calcine at 500° C. for 5 h to obtain a catalyst sample B with the weight percentage of a core layer being 64%, the weight percentage of a transition layer being 8% and the weight percentage of a shell layer being 28%.

Example 3

Take 5 g of 20 wt % Fe 1 wt % $K/SiO_2$ supported iron-based catalyst prepared using an—incipient wetness impregnation method. Admix the sample into 50 mL of aluminum isopropoxide trihydrate solution, continuously stir, then perform rotary evaporation to remove the solvent, dry and calcine to obtain an iron catalyst sample having an $Al_2O_3$ coating.

Next, admix the sample into 50 mL of solution containing tetrapropylammonium hydroxide template, ethyl orthosilicate, $Al_2O_3$, NaOH and $H_2O$ in a ratio of 0.3:1.0:0.05:0.010:130, stir for 4 h, then charge into a hydrothermal kettle, seal, heat to 180° C., and hydrothermally crystallize for 48 h. Filter the solid product after crystallization and cooling, wash till the pH value of the washing liquid is 8, then dry at 120° C. for 12 h, and calcine at 500° C. for 5 h to obtain a catalyst sample C with the weight percentage of a core layer being 74%, the weight percentage of a transition layer being 6% and the weight percentage of a shell layer being 20%.

Example 4

Take 5 g of the catalyst sample A in Example 1, admix into 5.2 mL of zinc nitrate solution by an incipient wetness impregnation method, perform rotary evaporation to dryness, dry at 120° C. for 12 h, and calcine at 500° C. for 5 h to obtain a catalyst sample containing 3% of metallic Zn element by weight in the shell layer molecular sieve; next, admix the sample into an n-hexane solution containing 2 wt % of ethyl orthosilicate, stir for 4 h, perform rotary evaporation to dryness, dry at 120° C. for 12 h, and calcine at 500° C. for 10 h to obtain a catalyst D.

Example 5

Take 2 g of the catalyst sample B in Example 2 to support a gallium nitrate solution by an ion exchange method, perform rotary evaporation to dryness, dry at 120° C. for 12 h, and calcine at 500° C. for 5 h to obtain a catalyst sample containing 2.5% of metallic Ga element by weight in the shell layer molecular sieve, next, admix the sample into 15 mL of n-hexane solution containing 2 wt % of ethyl orthosilicate, stir for 4 h, perform rotary evaporation to dryness, dry at 120° C. for 12 h, and calcine at 500° C. for 10 h to obtain a catalyst E.

Example 6

Take 2 g of the catalyst sample C in Example 3 to support a zinc nitrate solution by an ion exchange method, perform rotary evaporation to dryness, dry at 120° C. for 12 h, and calcine at 500° C. for 5 h to obtain a catalyst sample F containing 4% of metallic Zn element by weight in the shell layer molecular sieve.

Examples 7~11: Application of Invented Catalysts in Conversion of Synthesis Gas to Aromatic Hydrocarbons Mold the prepared catalyst under the pressure of 6.5 MPa, crush and sieve to obtain a sample of 40 to 60 meshes. Add 1.0 g of the catalyst into a continuous flow reactor, wherein the catalyst was pre-reduced with one or more of hydrogen, carbon monoxide, methane, ethane and ethylene gas for a certain period of time, and then cooled to the reaction temperature for continuous reaction. The reaction gas consisted of 45 vol % CO, 45 vol % $H_2$ and 4 vol % $N_2$, with $N_2$ as the internal standard gas for calculating the conversion rate of CO. The product was analyzed on line under atmospheric pressure by a gas chromatograph equipped with a thermal conductivity cell and a hydrogen ion flame detector after cold trap, and the product in the cold trap was analyzed off line by another gas chromatograph equipped with a hydrogen ion flame detector.

Example 7

Put 1 g of the catalysts A to F into a pressurized fixed bed reactor respectively, heat to 400° C. at 5° C./min in an $H_2$ atmosphere, and reduce under atmospheric pressure at the space velocity of 1000 $h^{-1}$ for 10 h. Then, cool, introduce a reaction gas for reaction, and continuously react at the pressure of 1.0 MPa, the space velocity of 5000 $h^{-1}$ and the temperature of 300° C. for 30 h, wherein the CO conversion rate and the selectivity of each product were shown in Table 1.

Example 8

Put 1 g of the catalyst D into a pressurized fixed bed reactor, heat to 400° C. at 5° C./min in an $H_2$ atmosphere, and reduce under atmospheric pressure at the space velocity of 1000 $h^{-1}$ for 10 h. Then, cool, introduce a reaction gas for reaction, continuously react at the pressure of 1.0 MPa, the space velocity of 5000 $h^{-1}$ and the temperatures of 250° C., 300° C., 350° C. and 400° C. for 30 h, and investigate the influence of the reaction temperatures. The CO conversion rate and the selectivity of each product were shown in Table 1.

Example 9

Put 1 g of the catalyst E into a pressurized fixed bed reactor, heat to 400° C. at 5° C./min in an $H_2$ atmosphere, and reduce under atmospheric pressure at the space velocity of 1000 $h^{-1}$ for 10 h. Then, cool, introduce a reaction gas for reaction, continuously react at the space velocity of 5000 $h^{-1}$, the temperature of 300° C. and the pressures of 0.5 MPa, 1.0 MPa, 2.0 MPa and 3.0 MPa for 30 h, and investigate the influence of the reaction pressures. The CO conversion rate and the selectivity of each product were shown in Table 1.

Example 10

Put 1 g of the catalyst D into a pressurized fluidized bed reactor and a slurry bed reactor respectively, heat to 400° C. at 5° C./min in an $H_2$ atmosphere, and reduce under atmospheric pressure at the space velocity of 1000 $h^{-1}$ for 10 h. Then, cool, introduce a reaction gas for reaction, and continuously react at the pressure of 1.0 MPa, the space velocity of 5000 $h^{-1}$ and the temperature of 300° C. for 30 h, wherein the CO conversion rate and the selectivity of each product were shown in Table 1. The results were used for comparing the reaction results of the catalyst in different reactors. The results showed that the results in the slurry bed reactor and the fluidized bed reactor were similar, but both are lower in the aromatic hydrocarbon selectivity than the fixed bed (Example 7).

Example 11

Put 1 g of the catalyst D into a pressurized fixed bed reactor, heat to 400° C. at 5° C./min in an $H_2$ atmosphere, and reduce under atmospheric pressure at the space velocity of 1000 $h^{-1}$ for 10 h. Then, cool, introduce a reaction gas for reaction, and continuously react at the pressure of 1.0 MPa, the space velocity of 5000 $h^{-1}$ and the temperature of 300° C. for 500 h. The CO conversion rate and the selectivity of each product were shown in Table 1.

Comparative Example 1

Tablet, mold, crush and sieve the precipitated FeMn catalyst and FeK/$SiO_2$ catalyst prepared in Example 1 and Example 3 respectively, add 1.0 g of respective catalyst of 40 to 60 meshes into a pressurized fixed bed reactor, heat to 400° C. at 5° C./min in an $H_2$ atmosphere, and reduce under atmospheric pressure at the space velocity of 1000 $h^{-1}$ for 10 h. Then, cool, introduce a reaction gas for reaction, and continuously react at the temperature of 300° C., the pressure of 1.0 MPa and the space velocity of 5000 $h^{-1}$ for 30 h, wherein the CO conversion rate and the selectivity of each product were shown in Table 2.

Comparative Example 2

Admix 5 g of the precipitated FeMn catalyst sample prepared in Example 1 into 50 mL of solution containing tetrapropylammonium hydroxide template, ethyl orthosilicate, $Al_2O_3$, NaOH and $H_2O$ in a ratio of 0.3:1.0:0:0.03:0.015:130, stir for 4 h, then charge into a hydrothermal kettle, seal, heat to 180° C., and hydrothermally crystallize for 48 h. Filter the solid product after crystallization and cooling, wash till the pH value of the washing liquid is 8, then dry at 120° C. for 12 h, and calcine at 500° C. for 5 h to obtain a catalyst sample G with the weight percentage of a core layer being 71% and the weight percentage of a shell layer being 29%. Tablet, mold, crush and sieve the catalyst G, add 1.0 g of the catalyst of 40 to 60 meshes into a pressurized fixed bed reactor and a slurry bed reactor respectively, heat to 400° C. at 5° C./min in an $H_2$ atmosphere, and reduce under atmospheric pressure at the space velocity of 1000 $h^{-1}$ for 10 h. Then, cool, introduce a reaction gas for reaction, and continuously react at the temperature of 300° C., the pressure of 1.0 MPa and the space velocity of 5000 $h^{-1}$ for 30 h, wherein the CO conversion rate and the selectivity of each product were shown in Table 2.

TABLE 1

Reaction performance of different catalysts for conversion of synthesis gas to aromatic hydrocarbons.

| Catalyst | Temperature °C. | Pressure/ MPa | CO conversion rate/% | Hydrocarbon product distribution (CO$_2$-free C-mol %) | | | | | | | | | |
|---|---|---|---|---|---|---|---|---|---|---|---|---|---|
| | | | | methane | olefin | alkane | benzene | toluene | xylene o- | m- | p- | A$_{9+}$ | other |
| A | 300 | 1 | 63 | 15.4 | 0.3 | 15.3 | 10.6 | 21.5 | 3.9 | 1.2 | 28 | 2.3 | 1.5 |
| B | 300 | 1 | 59 | 14.5 | 0.4 | 14.2 | 11.7 | 22.4 | 3.5 | 1.7 | 27.5 | 2.1 | 2 |
| C | 300 | 1 | 38.2 | 15.8 | 0.4 | 15.2 | 9.9 | 18.8 | 3.1 | 2.1 | 30.1 | 2.2 | 2.4 |
| D | 300 | 1 | 69.4 | 13.5 | 0.4 | 10.5 | 13.5 | 18.2 | 4.6 | 1.3 | 32.5 | 3.6 | 1.9 |
| E | 300 | 1 | 67 | 11.2 | 0.6 | 7.5 | 14.8 | 20.7 | 4.3 | 2.6 | 34.5 | 2.6 | 1.2 |
| F | 300 | 1 | 49.8 | 12.1 | 0.2 | 11.1 | 12.8 | 21.8 | 4.6 | 1.8 | 30.9 | 2.9 | 1.8 |
| D | 250 | 1 | 26.1 | 10.7 | 2.3 | 9.8 | 13.3 | 23.3 | 0.7 | 1.9 | 26.8 | 9.6 | 1.6 |
| D | 350 | 1 | 83 | 17 | 0.3 | 23.3 | 7.8 | 17.3 | 3.6 | 2.2 | 24.5 | 2.5 | 1.5 |
| D | 400 | 1 | 91 | 22.5 | 0.3 | 34.7 | 8.2 | 15.2 | 2.3 | 0.9 | 14.2 | 0.9 | 0.8 |
| E | 300 | 0.5 | 50 | 13 | 1.5 | 16 | 5.9 | 31.1 | 2.0 | 1.3 | 25.6 | 3 | 0.6 |
| E | 300 | 2 | 75.5 | 12.5 | 0.4 | 14.5 | 7.9 | 22.4 | 2.1 | 2.3 | 34.6 | 2.4 | 0.9 |
| E | 300 | 3 | 83 | 11 | 0.2 | 13 | 8.1 | 25.2 | 3.4 | 2.1 | 33.2 | 2.8 | 1 |
| D | 300 | 1 | 69.4 | 13.5 | 0.4 | 10.5 | 13.5 | 18.2 | 2.8 | 1.9 | 33.7 | 3.6 | 1.9 |
| D* | 300 | 1 | 56.5 | 15.5 | 1.2 | 12.5 | 8.8 | 18.2 | 3.5 | 0.6 | 27.1 | 8.2 | 4.4 |
| D** | 300 | 1 | 58.1 | 16.3 | 1.6 | 11.8 | 9.5 | 18.8 | 4.2 | 1.1 | 24.6 | 8.1 | 4 |
| D*** | 300 | 1 | 64 | 13.5 | 0.5 | 11 | 14.1 | 19.2 | 3.8 | 0.9 | 30.9 | 2.1 | 4 |

Reaction space velocity: 5000 h$^{-1}$; average value of reacting 10 to 30 h.
*, fluidized bed reactor; , slurry bed reactor; *, continuously reacting for 500 h.

TABLE 2

Comparative experiment results.

| Catalyst | Temperature °C. | Pressure/ MPa | CO conversion rate/% | Hydrocarbon product distribution (CO$_2$-free C-mol %) | | | | | | | | | |
|---|---|---|---|---|---|---|---|---|---|---|---|---|---|
| | | | | methane | olefin | alkane | benzene | toluene | xylene o- | m- | p- | A$_{9+}$ | other |
| FeMn | 300 | 1 | 57.6 | 14.5 | 45.6 | 34.9 | 0 | 0 | 0 | 0 | 0 | 0 | 5 |
| FeK/SiO$_2$ | 300 | 1 | 35.1 | 20.1 | 48 | 29.6 | 0 | 0 | 0 | 0 | 0 | 0 | 2.3 |
| G | 300 | 1 | 60 | 13 | 1.2 | 15 | 6.9 | 18.3 | 7.2 | 5.1 | 10.2 | 18.9 | 4.2 |
| G** | 300 | 1 | 62 | 14.5 | 1.5 | 14.5 | 7.3 | 16.2 | 4.5 | 6.4 | 9.4 | 20.9 | 4.8 |

Reaction space velocity: 5000 h$^{-1}$; average value of reacting 10 to 30 h.
**, slurry bed reactor.

It can be seen from the comparison of the examples and the comparative examples in Tables 1 and 2 that the catalyst containing the transition layer oxide and with the molecular sieve layer being modified internally and externally has higher selectivity to light aromatic hydrocarbons, the highest BTX selectivity is 76.9%, and particularly, the selectivity to xylene reaches 30% or above, accounting for 80 to 90% of the xylene. The catalysts with the molecular sieve layers not being modified internally and externally show more heavy aromatic hydrocarbon products.

The disclosure described and claimed herein is not to be limited in scope by the specific aspects herein disclosed. Any person skilled in the art can make modifications without departing from the spirit and scope of the disclosure. The scope of protection of the present disclosure should therefore be defined by the claims.

What is claimed is:

1. A multistage nanoreactor catalyst, comprising a structure of a core layer, a shell layer and a core-shell transition layer; wherein the core layer is an iron-based catalyst having Fischer-Tropsch activity, a weight of the core layer being 0.1% to 80% of a total weight of the catalyst; wherein the shell layer is a molecular sieve, a weight of the shell layer being 0.1% to 80% of the total weight of the catalyst; and wherein the core-shell transition layer is a porous oxide or porous carbon material, a weight of the transition layer being 0.01% to 35% of the total weight of the catalyst.

2. The multistage nanoreactor catalyst according to claim 1, wherein the iron-based catalyst having Fischer-Tropsch activity is a supported or unsupported catalyst comprising additives.

3. The multistage nanoreactor catalyst according to claim 1, wherein the molecular sieve is one or a mixture of two or more of ZSM-5, MCM-22, MCM-49, and SAPO-34 zeolite molecular sieves.

4. The multistage nanoreactor catalyst according to claim 1, wherein the molecular sieve comprises additives.

5. The multistage nanoreactor catalyst according to claim 4, wherein an outer surface of the molecular sieve has a silicon-oxygen compound.

6. The multistage nanoreactor catalyst according to claim 4, wherein the additives are selected from the group consisting of P, V, Cr, Mn, Fe, Co, Cu, Zn, Ga, Ge, Zr, Mo, Ru, Pd, Ag, W, Re and a combination thereof, and a weight of the additives is 0.01% to 35% of the weight of the shell layer.

7. The multistage nanoreactor catalyst according to claim 3, wherein the molecular sieve comprises additives.

8. The multistage nanoreactor catalyst according to claim 1, wherein the molecular sieve is a zeolite molecular sieve, and silica-alumina ratio of the zeolite molecular sieve is 10 to 500.

9. The multistage nanoreactor catalyst according to claim 1, wherein the porous oxide of the core-shell transition layer is selected from the group consisting of silicon oxide, aluminum oxide, zirconium oxide, magnesium oxide, zinc oxide, titanium oxide, calcium oxide and a combination thereof, and a thickness of the transition layer is 0.1 to 1000 nm.

10. The multistage nanoreactor catalyst according to claim 1, wherein an outer surface of the molecular sieve has a silicon-oxygen compound, wherein a weight of the silicon-oxygen compound is 0.01% to 20% of the weight of the shell layer.

* * * * *